(12) United States Patent
Centanni et al.

(10) Patent No.: US 8,025,807 B2
(45) Date of Patent: Sep. 27, 2011

(54) METHOD FOR TREATING RINSE WATER IN DECONTAMINATION DEVICES

(75) Inventors: Michael A. Centanni, Parma, OH (US); Kathleen A. Fix, Willoughby, OH (US); Christopher A. Jethrow, Maple Heights, OH (US)

(73) Assignee: American Sterilizer Company, Mentor, OH (US)

( * ) Notice: Subject to any disclaimer, the term of this patent is extended or adjusted under 35 U.S.C. 154(b) by 209 days.

(21) Appl. No.: 12/015,036

(22) Filed: Jan. 16, 2008

(65) Prior Publication Data
US 2009/0178981 A1    Jul. 16, 2009

(51) Int. Cl.
*C02F 1/78* (2006.01)
(52) U.S. Cl. ........ 210/750; 210/760; 210/764; 210/765; 210/766; 210/205; 261/DIG. 42
(58) Field of Classification Search .................. 210/746, 210/748, 750, 760, 764, 766, 180, 181, 192, 210/205, 209, 218, 219, 220, 739, 46, 765; 422/28, 29, 30, 31, 186.07–186.2; 261/DIG. 42, 261/19–74, 119–1, 121.1
See application file for complete search history.

(56) References Cited

U.S. PATENT DOCUMENTS

| 3,945,918 | A | * | 3/1976 | Kirk | 210/760 |
|---|---|---|---|---|---|
| 4,076,617 | A | * | 2/1978 | Bybel et al. | 261/124 |
| 4,431,545 | A | | 2/1984 | Pall et al. | 210/641 |
| 4,517,159 | A | * | 5/1985 | Karlson | 422/20 |
| 4,617,065 | A | | 10/1986 | Sundheimer | 134/25.4 |
| 4,767,528 | A | * | 8/1988 | Sasaki et al. | 210/192 |
| 5,487,814 | A | | 1/1996 | Santasalo | 203/2 |
| 7,135,142 | B2 | | 11/2006 | Burke et al. | 422/28 |
| 2005/0025663 | A1 | * | 2/2005 | Burke et al. | 422/28 |
| 2006/0280647 | A1 | | 12/2006 | Burke et al. | 422/28 |

FOREIGN PATENT DOCUMENTS

| EP | 0 945 140 | 9/1999 |
|---|---|---|
| JP | 411128158 | 5/1999 |

* cited by examiner

*Primary Examiner* — Nam Nguyen
*Assistant Examiner* — Lucas Stelling
(74) *Attorney, Agent, or Firm* — Kusner & Jaffe; Michael A. Centanni

(57) ABSTRACT

A processor for decontaminating devices is comprised of a chamber for holding devices and a circulation system to circulate a microbial decontamination fluid through the chamber. A water filtration system filters water used in the processor. The water filtration system has a water line connectable to a source of pressurized water. A water decontamination system fluidly communicates with the source of water and the processor. The water decontamination system has a water circulation path and a tank located within the water circulation path. Means are provided to circulate water along the water circulation path through the tank. A gas circulation path fluidly communicates with the tank. Conveying means is provided to convey gas along the gas circulation path through the tank. An ozone producing device is located along the gas circulation path to introduce ozone into gas flowing along the gas circulation path and through the tank.

12 Claims, 8 Drawing Sheets

METHOD FOR TREATING RINSE WATER IN DECONTAMINATION DEVICES

FIELD OF THE INVENTION

The present invention relates to microbial decontamination of medical, dental, pharmaceutical, veterinary or mortuary instruments and devices, and more particularly to a decontamination system for use in a liquid microbial decontamination system.

BACKGROUND OF THE INVENTION

Medical, dental, pharmaceutical, veterinary or mortuary instruments and devices that are exposed to blood or other body fluids require thorough cleaning and microbial decontamination or sterilization between each use. Liquid microbial decontamination systems are now widely used to clean and deactivate the microorganisms on instruments and devices that cannot withstand the high temperatures of a steam sterilization system. Liquid microbial decontamination systems typically operate by exposing the medical devices and/or instruments to a liquid disinfectant or sterilization composition, which may contain strong oxidants such as peracetic acid.

In such systems, the instruments or devices to be cleaned are typically placed within a chamber within the liquid microbial decontamination system, or in a container that is placed within the chamber. During a decontamination cycle, a liquid disinfectant is then circulated through a liquid circulation system that includes the chamber (and the container therein).

Following the decontamination cycle, a rinse solution, typically water, is circulated through the chamber to remove traces of the decontaminated microbial content and any particulate that may have accumulated on the instruments or devices during the decontamination cycle. It is important to have rinse water of high purity to ensure that the microbially decontaminated instruments and devices do not become re-contaminated during the rinse cycle.

The water used to rinse the instruments and devices generally passes through a filtration system to remove microorganism-related particulates from the water. However, filtration systems that are capable of filtering viruses are usually not used with liquid microbial decontamination systems. Thus, there is a possibility that a virus may pass through the filtration system and be introduced into the chamber during a rinse cycle.

The present invention overcomes these and other problems and provides a decontamination system for decontaminating viruses in water used in a microbial decontamination system.

SUMMARY OF THE INVENTION

In accordance with one embodiment of the present invention, there is provided a method of reducing viral levels in water used in a processor for decontaminating devices, the processor including a chamber for holding devices to be decontaminated, a circulation system for circulating a liquid sterilant or microbial decontamination fluid through the chamber, the chamber forming a part of the circulation system, a water filtration system for filtering water used in the processor, the water filtration system having a water line connectable to a source of pressurized water and a water decontamination system fluidly communicating with the source of water and the processor, the method comprising the steps of:

a) circulating a carrier gas along a first gas circulation path wherein the carrier gas is introduced into a predetermined volume of water;

b) introducing ozone into the carrier gas as the carrier gas flows along the first gas circulation path such that the ozone is introduced into the water;

c) establishing a concentration of ozone in the water between about 0.1 mg/L to about 2 mg/L;

d) mixing the water to achieve a uniform concentration of ozone in the water;

e) continuing steps b), c) and d) for at least about twenty (20) minutes;

f) separating the ozone from the water by heating and agitating the water;

g) collecting the ozone that is separated from the water into the carrier gas circulating along a second gas circulation path wherein the ozone separated from the water is conveyed by the carrier gas along the second gas circulation path;

h) destroying the ozone conveyed by the carrier gas at a location along the second gas circulation path, the location being downstream from the predetermined volume of water; and i) continuously agitating and heating the water until the concentration of the ozone in the water is below about 0.03 mg/L.

In accordance with another embodiment of the present invention, there is provided a method of reducing viral levels in water used in a processor for decontaminating devices, the processor including a chamber for holding devices to be decontaminated, a circulation system for circulating a liquid sterilant or microbial decontamination fluid through the chamber, the chamber forming a part of the circulation system, a water filtration system for filtering water used in the processor, the water filtration system having a water line connectable to a source of pressurized water and a water decontamination system fluidly communicating with the source of water and the processor, the method comprising the steps of:

a) circulating a carrier gas along a first gas circulation path wherein the carrier gas is introduced into a predetermined volume of water;

b) introducing ozone into the carrier gas as the carrier gas flows along the first gas circulation path such that the ozone is introduced into the water;

c) establishing a concentration of ozone in the water between about 0.1 mg/L to about 2 mg/L;

d) mixing the water to achieve a uniform concentration of ozone in the water; and e) continuing steps b), c) and d) for at least about twenty (20) minutes.

In accordance with yet another embodiment of the present invention, there is provided a method of reducing viral levels in water used in a processor for decontaminating devices, the method comprising the steps of:

a) circulating a carrier gas along a first gas circulation path wherein the carrier gas is introduced into a predetermined volume of water;

b) introducing ozone into the carrier gas as the carrier gas flows along the first gas circulation path such that the ozone is introduced into the water;

c) establishing a concentration of ozone in the water between about 0.1 mg/L to about 2 mg/L;

d) mixing the water to achieve a uniform concentration of ozone in the water;

e) continuing steps b), c) and d) for at least about twenty (20) minutes;

f) separating the ozone from the water by heating and agitating the water;

g) collecting the ozone that is separated from the water into the carrier gas circulating along a second gas circulation path wherein the ozone separated from the water is conveyed by the carrier gas along the second gas circulation path;

h) destroying the ozone conveyed by the carrier gas at a location along the second gas circulation path, the location being downstream from the predetermined volume of water; and i) continuously agitating and heating the water until the concentration of the ozone in the water is below about 0.03 mg/L.

In accordance with yet another embodiment of the present invention, there is provided a method of reducing viral levels in water used in a decontamination apparatus, the decontamination apparatus including a chamber for holding devices to be decontaminated, a circulation system for circulating a decontaminant through the chamber, the chamber forming a part of the circulation system, a water line connectable to a source of pressurized water and a water decontamination system fluidly communicating with the source of water and the decontamination apparatus, the method comprising the steps of:

a) circulating a carrier gas along a first gas circulation path wherein the carrier gas is introduced into a predetermined volume of water;

b) introducing ozone into the carrier gas as the carrier gas flows along the first gas circulation path such that the ozone is introduced into the water;

c) establishing a concentration of ozone in the water between about 0.1 mg/L to about 2 mg/L;

d) mixing the water to achieve a uniform concentration of ozone in the water;

e) continuing steps b), c) and d) for at least about five (5) minutes;

f) separating the ozone from the water by heating and agitating the water;

g) collecting the ozone that is separated from the water into the carrier gas circulating along a second gas circulation path wherein the ozone separated from the water is conveyed by the carrier gas along the second gas circulation path;

h) destroying the ozone conveyed by the carrier gas at a location along the second gas circulation path, the location being downstream from the predetermined volume of water; and i) continuously agitating and heating the water until the concentration of the ozone in the water is below about 0.03 mg/L.

In accordance with still another embodiment of the present invention, there is provided a processor for decontaminating devices. The processor has a chamber for holding devices to be decontaminated and a circulation system to circulate a liquid sterilant or microbial decontamination fluid through the chamber. The chamber forms a part of the circulation system. A water filtration system is provided to filter water used in the processor. The water filtration system has a water line connectable to a source of pressurized water. A water decontamination system is provided to fluidly communicate with the source of water and the processor. The water decontamination system has a water circulation path to fluidly communicate with the source of water and the processor. A tank is located within the water circulation path. The tank is dimensioned to retain a predetermined volume of water. Means are provided to circulate water along the water circulation path through the tank. A gas circulation path is provided to fluidly communicate with the tank. Conveying means is provided to convey gas along the gas circulation path through the tank. An ozone producing device is located along the gas circulation path to introduce ozone into gas flowing along the gas circulation path and through the tank.

One advantage of the present invention is the provision of a rinse water decontamination system for a reprocessing system.

Another advantage of the present invention is the provision of a rinse water decontamination system as described above that reduces the likelihood of viral contamination of rinse water as a result of viral contamination from a water source.

These and other advantages will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figure 1:
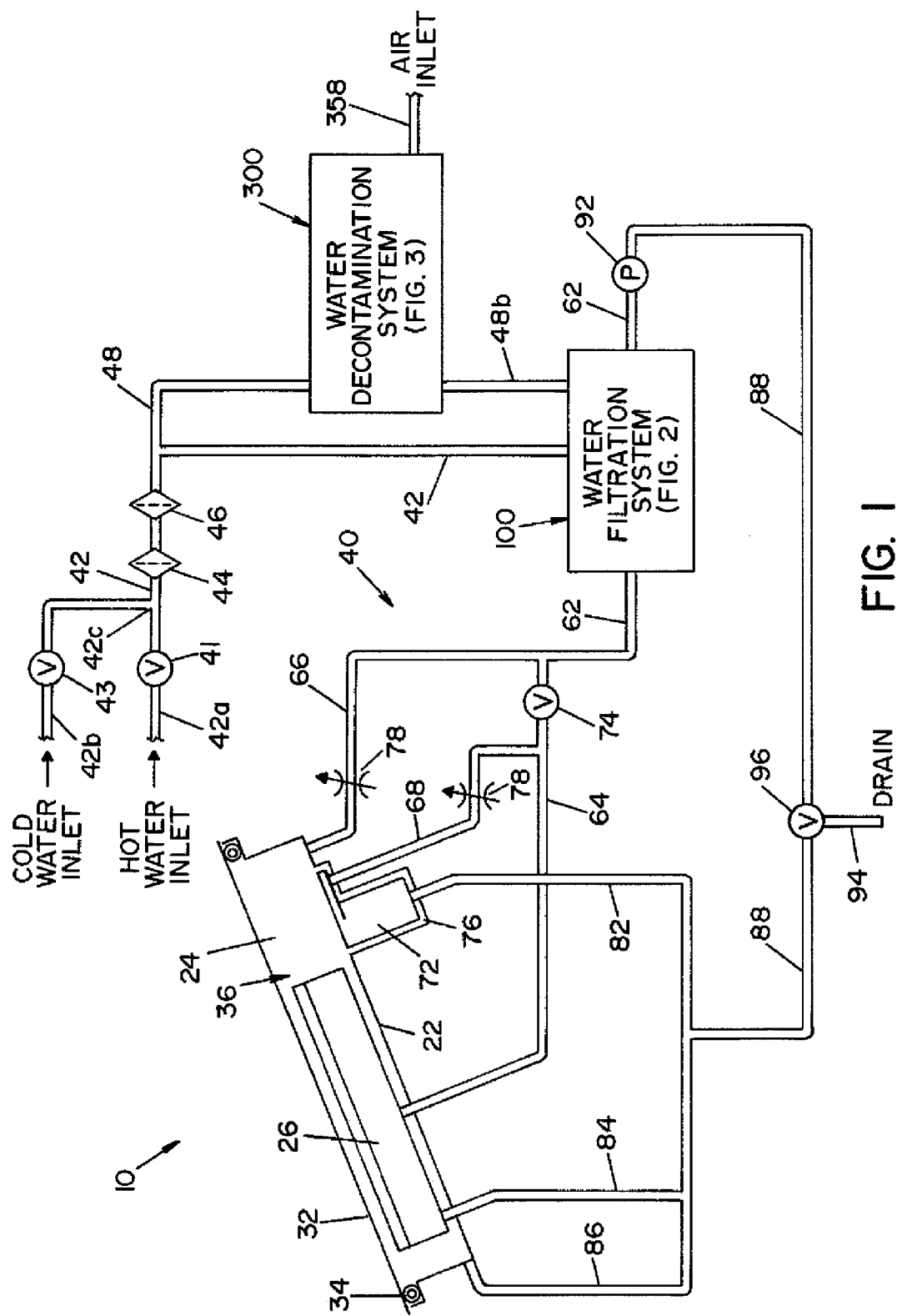
FIG. 1 is a schematic view of a microbial decontamination system with a water decontamination system.

Referring now to the drawings wherein the showings are for the purpose of illustrating one embodiment of the invention only, and not for the purpose of limiting same, FIG. 1 shows a simplified, schematic piping diagram of a microbial decontamination apparatus 10 illustrating one embodiment of the present invention. Apparatus 10 may be a commercial or industrial washing machine wherein a decontaminant is used to decontaminate the contents of the commercial or industrial washer. The decontaminant used in the commercial or industrial washing machine may be a soap.

A panel 22, that is part of a housing structure (not shown), defines a recess or cavity 24 dimensioned to receive items or instruments to be microbially decontaminated. In the embodiment shown, a tray or container 26 is provided to receive the devices or instruments to be decontaminated. Container 26 is dimensioned to be received within recess or cavity 24, as illustrated in FIG. 1.

A manually operable lid 32 is movable between an opened position allowing access to cavity 24, and a closed position (shown in FIG. 1) closing or covering cavity 24. A seal element 34 surrounds cavity 24 and forms a fluid-tight, i.e., an airtight and liquid-tight, seal between lid 32 and panel 22 when lid 32 is in a closed position. Latch means (not shown)

are provided for latching and securing lid 32 in a closed position during a decontamination cycle. Cavity 24 essentially defines a chamber 36 when lid 32 is in a closed position.

A fluid circulation system 40 provides the microbial decontamination fluid to chamber 36 and is further operable to circulate the microbial decontamination fluid through chamber 36. Fluid circulation system 40 includes a water inlet line 42 that is connected at a junction 42c to a hot water line 42a and a cold water line 42b. Hot water line 42a is connected to a source of heated water (not shown). A hot water valve 41 is located in hot water line 42a to control the flow of water therethrough. Cold water line 42b is connected to a source of cold water (not shown). In one embodiment, the source of cold water provides water that is less than about 43° C. In another embodiment, the source of cold water provides water that is between about 20° C. and about 40° C. A cold water valve 43 is located in cold water line 42b to control the flow of water therethrough.

A pair of filter elements 44, 46 are provided in water inlet line 42 at a location downstream of junction 42c to filter out large contaminants that may exist in the incoming water. Filters 44, 46 are size exclusion filter elements, which remove particles of a certain size. Filter element 46 preferably filters out smaller particles than filter element 44. Filter element 44 preferably filters out particles of about 3 micrometers ($\mu$m) or larger, and filter element 46 preferably filters out particles of about 0.1 micrometers ($\mu$m) or larger. Pressure sensors (not shown) may be provided to monitor pressure drops across filter elements 44, 46, a change in the pressure drop across a filter element being indicative of clogging, rupturing or the like. Basically, filter elements 44, 46 are provided to filter out particles found in the water source used to supply apparatus 10.

Figure 2:
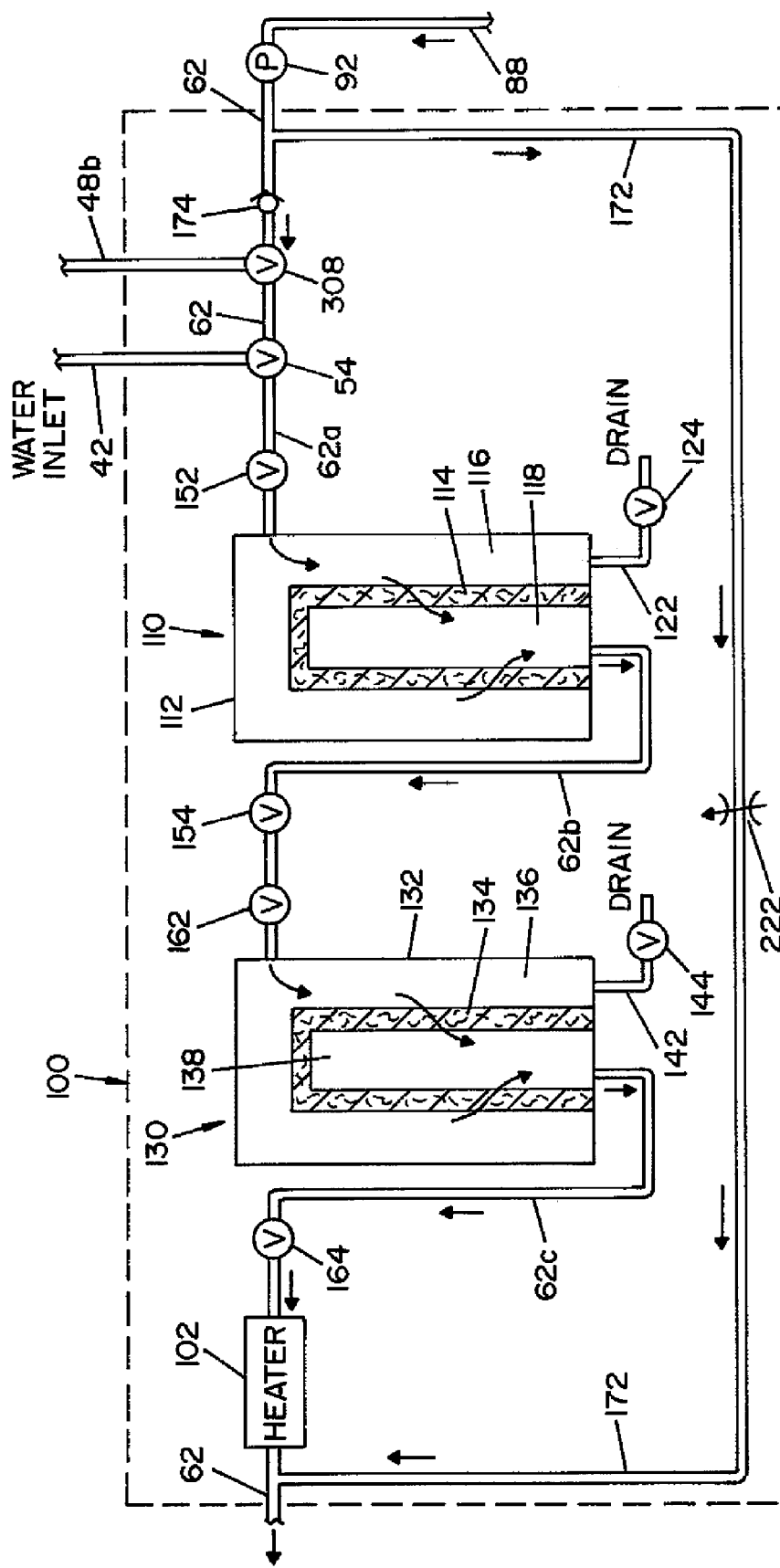
FIG. 2 is a schematic view of a filtration system.

Referring to FIG. 2, a water valve 54 controls the flow of water from water inlet line 42 to a system feeder line 62. System feeder line 62 includes a filtration system 100 to filter out microscopic organisms and particles from the incoming water so as to provide microbially decontaminated or sterile water to fluid circulation system 40. System feeder line 62 splits into a first branch feeder line 64 and a second branch feeder line 66. First branch feeder line 64 communicates with container 26 within chamber 36. Second branch feeder line 66 is connected to chamber 36 itself. A secondary branch feeder line 68 splits off of first branch feeder line 64 and is directed to the inlet portion of chemical delivery dispensing container 72 that contains chemical reagents that, when combined with water, form the antimicrobial fluid used in the decontamination system. A valve 74 controls flow through first branch feeder line 64 and through secondary branch feeder line 68 to chemical dispensing container 72. Chemical dispensing container 72 is located within a well 76 formed within panel 22 of the housing. Flow restrictors 78 in second branch feeder line 66 and secondary branch feeder line 68 regulate fluid flow therethrough.

A branch return line 82 extends from chemical dispensing container 72 and is connected to a system return line 88. Likewise, branch fluid return lines 84, 86 extend from container 26 and chamber 36 respectively and are connected to system return line 88. System return line 88 connects back with water inlet line 42 and fluid feeder line 62, as illustrated in FIG. 1. A pump 92 is located within system return line 88. Pump 92 is operable to circulate fluid through fluid circulation system 40. A drain line 94 is connected to system return line 88. A drain valve 96 controls fluid flow to drain line 94.

Referring now to FIG. 2, water filtration system 100 is best seen. Water filtration system 100 is located within fluid feeder line 62 and includes two filter elements 114 and 134, shown as part of filter assemblies 110, 130. Filter elements 114, 134 are located in series in fluid feeder line 62. A first section 62a of fluid feeder line 62 communicates with water inlet line 42 to the inlet side of first filter assembly 110. A second section 62b of fluid feeder line 62 connects the outlet side of first filter assembly 110 to the inlet side of second filter assembly 130. A third section 62c of fluid feeder line 62 connects the outlet side of second filter assembly 130 to a heater 102 that is schematically illustrated in FIG. 2. Heater 102 is capable of heating water flowing through third section 62c of fluid feeder line 62 to a temperature of at least about 50° C.

First filter assembly 110 includes housing 112 and an internal filter element 114. Filter element 114 is a bacterial retentive size exclusion filter that preferably filters out microorganism particles that are nominally 0.12 micrometers ($\mu$m) or greater. Filter element 114 may include a cylindrical support layer (not shown), such as a polypropylene, a homopolymer surrounded by a filter membrane, such as a hydrophilic polyvinylidene difluoride (PVDF) or a polyethersulfone (PES) membrane. The filter membrane may be in the form of a capillary tube or hollow fiber member (or "fiber"), or in the form of a tubular sheath of a film formed either on the inner or outer surface of a tubular macroporous support, or a laminate sheet or film, or a laminate film deposited on the porous support. Suitable filter elements are obtainable from PTI Technologies of Oxnard, Calif.

Filter element 114 defines an annular outer chamber 116 and inner chamber 118. Outer chamber 116 represents the upstream, pre-filtration side of filter element 114, and inner chamber 118 of the filter assembly represents the downstream, filtered side of filter element 114. As shown in the drawings, first section 62a of fluid feeder line 62 communicates with outer chamber 116 of first filter assembly 110, and second section 62b of feeder line 62 communicates with inner chamber 118 of first filter assembly 110. A drain line 122 communicates with outer chamber 116 of first filter assembly 110. Valve 124 is located within drain line 122 to regulate flow from first filter assembly 110 to a drain.

Second filter assembly 130 includes housing 132 and an internal filter element 134. Filter element 134 is a bacterial retentive size exclusion filter that preferably filters out microorganism particles that are nominally 0.12 micrometers ($\mu$m) or greater. Filter element 134 may include a cylindrical support layer, such as a polypropylene, a homopolymer surrounded by a filter membrane, such as a hydrophilic polyvinylidene difluoride (PVDF) or a polyethersulfone (PES) membrane. The filter membrane may be in the form of a capillary tube or hollow fiber member (or "fiber"), or in the form of a tubular sheath of a film formed either on the inner or outer surface of a tubular macroporous support, or a laminate sheet or film, or a laminate film deposited on the porous support. Suitable filter elements are obtainable from PTI Technologies of Oxnard, Calif. Filter element 134 defines an annular outer chamber 136 and inner chamber 138. Outer chamber 136 represents the upstream, pre-filtration side of filter element 134, and inner chamber 138 of filter assembly 130 represents the downstream, filtered side of filter element 134. As shown in the drawings, second section 62b of feeder line 62 communicates with outer chamber 136 of second filter assembly 130 and third section 62c of feeder line 62 communicates with inner chamber 138 of second filter assembly 130. Drain line 142 communicates with outer chamber 136 of second filter assembly 130. A valve 144 is located within drain line 142 to regulate flow from second filter assembly 130 to a drain.

Both first and second filter assemblies 110, 130 are preferably pre-sterilized or microbially decontaminated, prior to installation, so that the contents of filter assemblies 110, 130 are free of microbial contaminants. As will be described in greater detail below, filter assemblies 110, 130 are microbially decontaminated or sterilized during each subsequent processing phase.

A first pair of valves 152, 154 is located in fluid feeder line 62 to enable isolation of first filter assembly 110. In this respect, valve 152 is located within first section 62a of fluid feeder line 62 at the inlet side of first filter assembly 110, and valve 154 is located in feeder line section 62b at the outlet side of first filter assembly 110. Similarly, a second pair of valves 162, 164 is located in fluid feeder line 62 to enable isolation of second filter assembly 130. In this respect, valve 162 is located in fluid line section 62b at the inlet side of second filter assembly 130, and valve 164 is located in fluid feeder line section 62c at the outlet side of second filter assembly 130.

A filter bypass line 172 communicates with fluid feed line 62 on opposite sides of first and second filter assemblies 110, 130. Specifically, one end of bypass line 172 is connected to fluid feed line 62 between pump 92 and the location where water inlet line 42 connects to fluid feed line 62. A directional check valve 174 is located between water inlet line 42 and filter bypass line 172 to prevent incoming water from communicating with filter bypass line 172, as shall be described in greater detail below. The other end of filter bypass line 172 communicates with feeder line 62 downstream of filter assemblies 110, 130 and heater 102.

FIG. 1 shows a water decontamination system 300 to reduce the level of viral particles or viruses in water used in microbial decontamination apparatus 10. It is contemplated that decontamination system 300 may be used to reduce the level of viral particles or viruses in water used in microbial decontamination apparatus 10, when such water does not meet potable water standards. Water decontamination system 300 is connected to apparatus 10 by means of a second water inlet line 48. Second water inlet line 48 is connected at one end to water inlet line 42 at a location downstream of filter elements 44 and 46 and is connected at another end to system feeder line 62 at a location between directional check valve 174 and water valve 54. As shown in FIG. 2, valve 308 is located at a location where second water inlet line 48 connects to system feeder line 62. Valve 308 is a two-way valve that is operable to control the flow of water from second water inlet line 48 to system feeder line 62. In this respect, water that enters apparatus 10 through second water inlet line 48 passes through filter elements 44, 46, water decontamination system 300 and water filtration system 100.

Referring now to FIG. 3, water decontamination system 300 is best seen. Water decontamination system 300 is generally comprised of a fluid-holding tank 302. Tank 302 defines an internal cavity 304 that is capable of holding at least a predetermined volume of fluid. An inlet line 312 is connected at one end of tank 302 and at another end to second water inlet line 48. A portion of inlet line 312 extends into cavity 304 of tank 302. Inlet line 312 is connected to second water inlet line 48 at a location between filter element 46 and the location where second water inlet line 48 connects to system feeder line 62. A valve 306 is located at the location wherein inlet line 312 connects to second water inlet line 48. Valve 306 is a three-way valve that is operable to selectively control the flow of water along second water inlet line 48. An outlet line 313 is connected at one end to tank 302 and at another end to second water inlet line 48 at a junction between valve 306 and valve 308.

A plurality of nozzles 318 are located on the portion of inlet line 312 that extends into cavity 304 of tank 302. Nozzles 318 have a combined cross-sectional area smaller than a cross-sectional area of inlet line 312.

Second water inlet line 48 is generally comprised of a first portion 48*a* and a second portion 48*b*. Portion 48*a* is defined as a portion of second water inlet line 48 that is between valve 306 and the junction where outlet line 313 connects to second water inlet line 48. Portion 48*b* is defined as a portion of second water inlet line 48 between valve 308 and the junction where outlet line 313 connects to second water inlet line 48. Portion 48*b* is dimensioned to be as short as possible to minimize the volume of water therein.

A fill switch 326 is located in cavity 304 of tank 302. Fill switch 326 is operable to provide a signal to the system controller when a volume of water in cavity 304 has reached a desired volume. Fill switch 326 is preferably a conventional float switch.

A sensor 328 is located in cavity 304 of tank 302. Sensor 328 is operable to provide a signal to the system controller that is proportional to a concentration of ozone in water located in tank 302. Sensor 328 is located in tank 302 at a location below fill switch 326.

An agitating device 332 is located within cavity 304 to circulate water within cavity 304. Agitating device 332 is operable between an "OFF" state, a first "ON" state and a second "ON" state. The first "ON" state causes less circulation in tank 302 than the second "ON" state. In the embodiment shown, agitating device 332 is comprised of a mixing blade that is connected to a motor 334. Motor 334 is located outside of tank 302 and is operable to rotate the mixing blade thereby circulating water in tank 302.

A temperature measuring device 336 is located within cavity 304 to measure a temperature of water therein. Temperature measuring device 336 is operable to provide a signal to the system controller proportional to water temperature within tank 302.

A pressure compensation device 338 is located on tank 302 to allow gas to escape but prevents other external contaminants from entering when the pressure in tank 302 is greater than an external pressure. Pressure-compensation device 338 also allows gas to enter tank 302 when the pressure in tank 302 is less than an external pressure. Pressure compensation device 338 includes a filter membrane (not shown) to remove debris and contamination from gas flowing therethrough.

A drain line 322 is connected to a lower part of tank 302 at one end. Drain line 322 is connected to a low point in tank 302 so that no residual water remains in tank 302 when drain line 322 is fluidly communicating with the drain. A drain valve 324 is located within drain line 322 to control the flow of water therethrough.

A pump 314 is located in outlet line 313 downstream of tank 302 and upstream of the junction where outlet line 313 connects to second water inlet line 48. Pump 314 is operable to circulate water along outlet line 313. Pump 314 is capable of pumping between about 1 gallon per minute and about 5 gallons per minute. In one embodiment, pump 314 pumps about 3 gallons per minute.

A heating device 316 is located within outlet line 313 between pump 314 and the junction where outlet line 313 connects to second water inlet line 48. Heating device 316 is operable to heat water flowing therethrough. For a given heating device 316, the time to heat water in tank 302 will depend upon the flow rate of water through heating device 316 and the amount of water in tank 302. For a fixed amount of water in tank 302 and a fixed flow rate, heating device 316 is capable of heating water in decontamination system 300 from about 25° C. (77° F.) to about 45° C. (113° F.) in less than about thirty (30) minutes. In one embodiment, heating device 316 is an instantaneous water heater manufactured by Eemax, Inc. of Oxford, Conn., model EX320T2T having a power output of 32 kW and providing a temperature rise of about 73° F. at a flow rate of about three (3) gallons per minute. In this embodiment, water enters the instantaneous water heater at about 25° C. (77° F.) and exits at about 67° C. (150° F.) when flowing at about 3 gallons per minute. In this respect, the time to heat water in tank 302 to a desired temperature will depend upon the amount of water in tank 302. In an alternative embodiment (not shown), heating device 316 is located within internal cavity 304 of tank 302. In this alternative embodiment, heating device 316 is preferably a submersion heater.

A branch line 342 is connected at a first end to an upper portion of tank 302 and at a second end to a lower portion of tank 302. The second end of branch line 342 extends into cavity 304 and terminates at a location below a level of water in tank 302, as shall be described in greater detail below.

A blower 344 is located in branch line 342 to circulate gas along branch line 342. A motor 346 is attached to blower 344 and is operable to turn vanes (not shown) in blower 344.

An ozone-producing device 348 is located in branch line 342 at a location downstream of blower 344 to introduce ozone into gas passing therethrough. In one embodiment, ozone-producing device 348 is an ultraviolet (UV) light source. Ozone is created when oxygen-containing gas is exposed to a UV light source at a wavelength of less than about 210 nm. In another embodiment, ozone-producing device 348 uses a parallel plate capacitor which is able to attain a high voltage, usually greater than 5,000 volts. In this respect, ozone is created when oxygen-containing gas is exposed to a high electrical potential. In another embodiment, ozone-producing device 348 is corona discharge device. In this respect, ozone is created when a spark is discharged across a gas containing oxygen. In another embodiment, ozone-producing device 348 is an electrolytic cell for the production of ozone from water.

A directional check valve 364 is located in branch line 342 at a location downstream of ozone producing device 348. Directional check valve 364 is operable to allow gas to flow from branch line 342 to tank 302 but prevents fluid from flowing from tank 302 to the portion of branch line 342 upstream of where directional check valve 364 is located.

An ozone-dissolution device 366 is located on the second end of branch line 342 located in tank 302. Dissolution device 366 is in fluid communication with branch line 342 and allows gas to flow therethrough. In one embodiment, dissolution device 366 is a metal or ceramic filter with small holes formed therein. In another embodiment, dissolution device 366 is a Venturi-type device (not shown) wherein pressurized water flows therethrough to aid in the dissolution of the gas entering the Venturi device.

Figure 3:
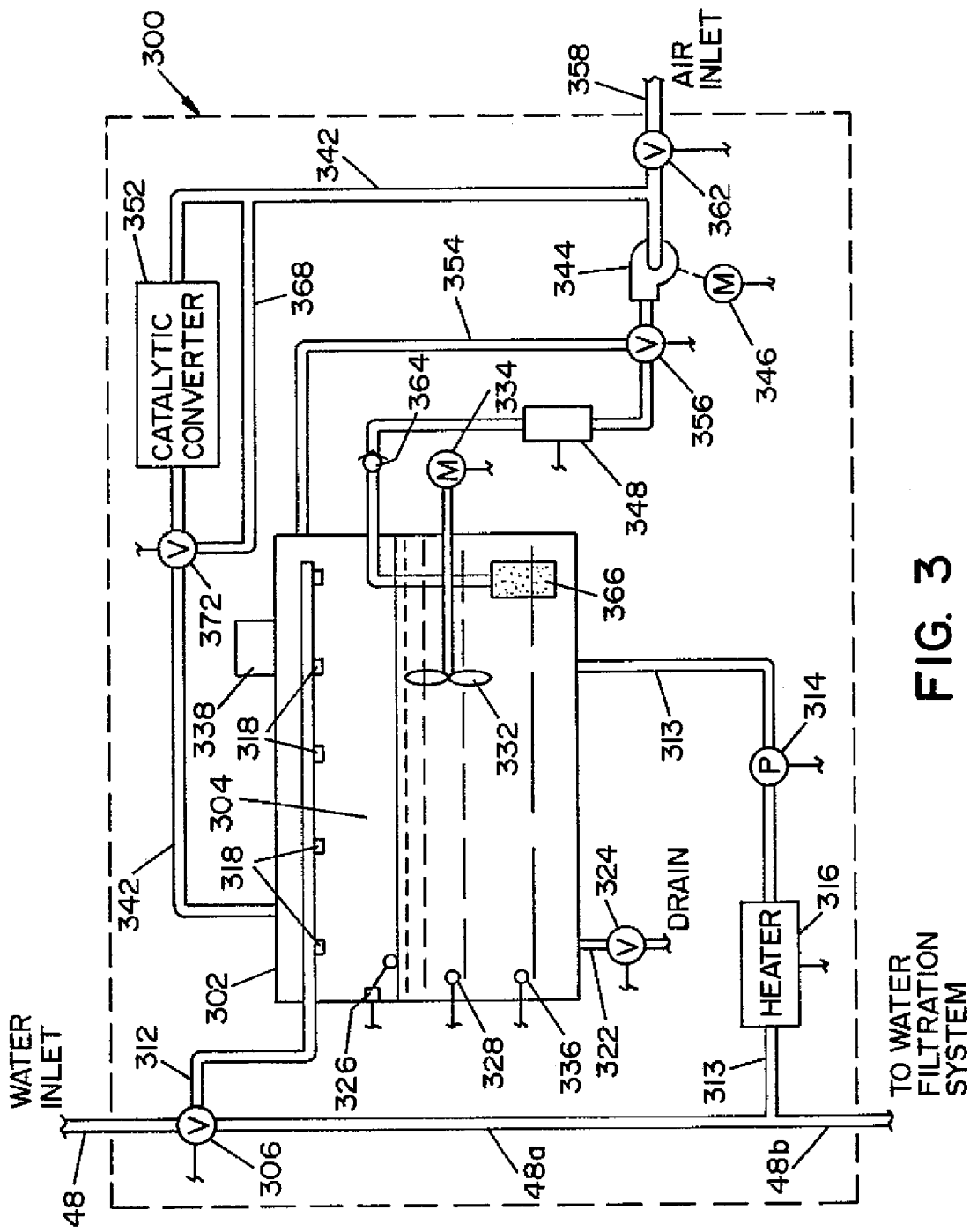
FIG. 3 is a schematic view of a water decontamination system.

A valve 356 is located within branch line 342 between blower 344 and ozone-producing device 348. Valve 356 is located upstream of ozone-producing device 348, as shown in FIG. 3. Valve 356 is a three-way valve operable to control flow through branch line 342 and a first bypass line 354. First bypass line 354 is connected at a first end to valve 356 and at second end to an upper portion of tank 302. When valve 356 is in a first position, a portion of branch line 342 upstream of valve 356 is in fluid communication with first bypass line 354 and not ozone-producing device 348. When valve 356 is in a second position, a portion of branch line 342 upstream of valve 356 is in fluid communication with ozone-producing device 348 and not first bypass line 354.

An ozone destruction device 352 is located in branch line 342 at a location downstream of the second end of branch line 342 and upstream of blower 344. Ozone destruction device 352 is operable to reduce the concentration of ozone in gas passing therethrough to below about 0.3 ppm. In one embodiment, ozone destruction device 352 is catalyst that is made of platinum or palladium. In another embodiment, ozone destruction device 352 is a catalyst made of individual or mixed metal oxides (e.g., aluminum oxide, copper oxide and/or manganese oxide) or hydroxides and peroxides. In yet another embodiment, ozone destruction device 352 is a UV light source that operates at a wavelength of 254 nm.

A bypass valve 372 is located within branch line 342 between tank 302 and ozone destruction device 352. Valve 372 is located upstream of ozone destruction device 352, as shown in FIG. 3. Valve 372 is a three-way valve operable to control flow through branch line 342 and a second bypass line 368. Second bypass line 368 is connected at one end to valve 372 and is connected at its other end to branch line 342 at a location between ozone destruction device 352 and blower 344. When bypass valve 372 is in a first position, a portion of branch line 342 upstream of valve 372 is in fluid communication with second bypass line 368 and not ozone destruction device 352. When bypass valve 372 is in a second position, a portion of branch line 342 upstream of valve 372 is in fluid communication with ozone destruction device 352 and not second bypass line 368.

A gas inlet line 358 is connected to branch line 342 at a location upstream of blower 344 and downstream of ozone destruction device 352. Gas inlet line 358 is connected on another end to a source of pressurized gas. A gas inlet valve 362 is located in gas inlet line 358 to control the flow of gas along gas inlet line 358. In one embodiment of the present invention, the pressurized gas is air.

A system microprocessor (not shown) controls the operation of circulation system 40 and water decontamination system 300 and the valves therein. The operation of circulation system 40 includes a fill phase, a chemical introduction and exposure phase, a drain phase and one or more rinse phases. The operation of water decontamination system 300 includes a fill phase, an ozone generation phase, an exposure phase, an ozone destruction phase, one or more delivery phases and a drain phase.

The present invention shall now further be described with reference to the operation of apparatus 10 and water decontamination system 300. One or more items to be microbially decontaminated or sterilized, such as medical, dental, pharmaceutical, veterinary or mortuary instruments or other devices are loaded into chamber 36. In the embodiment shown, the items would be loaded into container 26, which in turn would be placed into chamber 36. The items may be supported in a tray, basket, cartridge or the like (not shown) within chamber 36 or container 26.

The items are microbially decontaminated or sterilized with a microbial decontamination fluid, such as a peracetic acid solution, which in one embodiment is formed by exposing and mixing chemical reagents within the chemical dispensing device 72 with incoming water.

During a fill phase of apparatus 10, drain valve 96 in circulation system 40 is closed, and water valve 54 in inlet line 42 and hot water valve 41 in hot water line 42a are opened to allow heated water to flow along inlet line 42 and enter circulation system 40. Incoming water is first filtered by filter elements 44, 46 in water inlet line 42 that, as indicated above, remove particles above a certain size. Filter elements 44, 46 are sized to successively filter out smaller sized particles. The incoming water passes through the valve 54 and enters circulation system 40. The incoming water is then filtered by filter assemblies 110, 130 in feeder line 62 and proceeds to fill circulation system 40, chamber 36 and container 26.

Check valve 174 between water inlet valve 54 and filter bypass line 172 causes all of the incoming water to flow through the first and second filter assemblies 110, 130, thereby insuring filtration of the water flowing into apparatus 10.

The incoming water is under pressure from an external source, and forces air in fluid circulation system 40, chamber 36 and container 26 to an over-flow/air device (not shown) that is typically located at the highest point of apparatus 10. Air within the system migrates toward the over-flow device.

The presence of the water flowing through the over-flow block is indicative that apparatus 10 is filled with water. The system controller then causes hot water valve 41 and water valve 54 to close, thereby stopping the flow of water into apparatus 10, i.e., into fluid circulation system 40, chamber 36 and container 26. The foregoing description basically describes a water fill phase of apparatus 10.

Once apparatus 10 is filled, the system controller initiates a chemical introduction and exposure phase of operation, wherein pump 92 is energized to circulate water through circulation system 40, chamber 36 and container 26. Valve 74 in first branch feeder line 64 is opened to create flow through chemical dispensing container 72. The water and chemical reagents within chemical dispensing container 72 form a microbial decontamination fluid that, as indicated above, in one embodiment of the invention, is peracetic acid. In one embodiment of the present invention, chemical reagents within chemical dispensing container 72 are dry prior to mixing with the water. The decontamination fluid formed from the chemical reagents flows into circulation system 40, wherein it is circulated through circulation system 40, chamber 36 and container 26 by pump 92. In this respect, as indicated in the drawings, a portion of the microbial decontamination or sterilant fluid flows into chamber 36 around container 26 and a portion of the microbial decontamination fluid flows into and through container 26 and the items contained therein.

As indicated by the arrows in FIG. 2, a portion of the circulated decontamination fluid flows through filter bypass line 172 and a portion of the decontamination fluid flows through feed line 62 through filter assemblies 110, 130. The amount of fluid flowing through the respective portions of the system may be controlled by a regulating valve 222 located within filter bypass line 172 or fluid feed line 62. Preferably, a major portion of the decontamination fluid flows through filter bypass line 172. The portion of the decontamination fluid flowing through filter feed line 62 and through the first and second filter assemblies 110, 130 are preferably such to insure decontamination of filter elements 114, 134 by exposure to the decontamination fluid. In this respect, the flow of the decontamination fluid through filter assemblies 110, 130 microbially deactivates or sterilizes filter elements 114, 134 and inactivates any microbial contamination that may have entered into filter assemblies 110, 130 during the water fill phase. Thus, during each operation of apparatus 10, filter elements 114, 134 are exposed to a microbial decontamination or sterilant fluid to microbially deactivate or sterilize the same. Moreover, the microbial decontamination fluid that flows throughout the closed-loop, fluid circulation system 40 during a chemical introduction and exposure phase, effectively decontaminates fluid circulation system 40, and the components and fluid conduits forming the same. In other words, fluid circulation system 40 is decontaminated during each decontamination cycle.

After a predetermined exposure period, a drain phase is initiated. Drain valve 96 is opened and the microbial decontamination fluid is drained from the re-circulation system, chamber 36 and container 26.

After the microbial decontamination fluid has been drained from apparatus 10, one or more rinsing phases are performed to rinse any residual microbial decontamination fluid and any residual matter from the decontaminated items. Prior to a rinse phase of apparatus 10, water decontamination system 300 will have performed a decontamination cycle to prepare treated water to be delivered to apparatus 10, as described below.

As described above, system microprocessor (not shown) controls the operation of water decontamination system 300 and the components therein. The operation of decontamination system 300 includes a fill phase, an ozone generation phase, an exposure phase, an ozone destruction phase, one or more delivery phases and a drain phase.

Prior to a fill phase of water decontamination system 300, valve 306 is in a closed state wherein second water inlet line 48 is not in fluid communication with portion 48a or inlet line 312. Valve 308 is in a closed state wherein second water inlet line 48 is not in fluid communication with system feeder line 62. Valve 356 is in a second position wherein first bypass line 354 is not in fluid communication with branch line 342. Valve 372 is in a first position wherein a portion of branch line 342 upstream of valve 372 is in fluid communication with second bypass line 368. Pump 314, heating device 316, agitating device 332, ozone producing device 348, blower 346, and ozone destruction device 352 are all de-energized.

Figure 4:
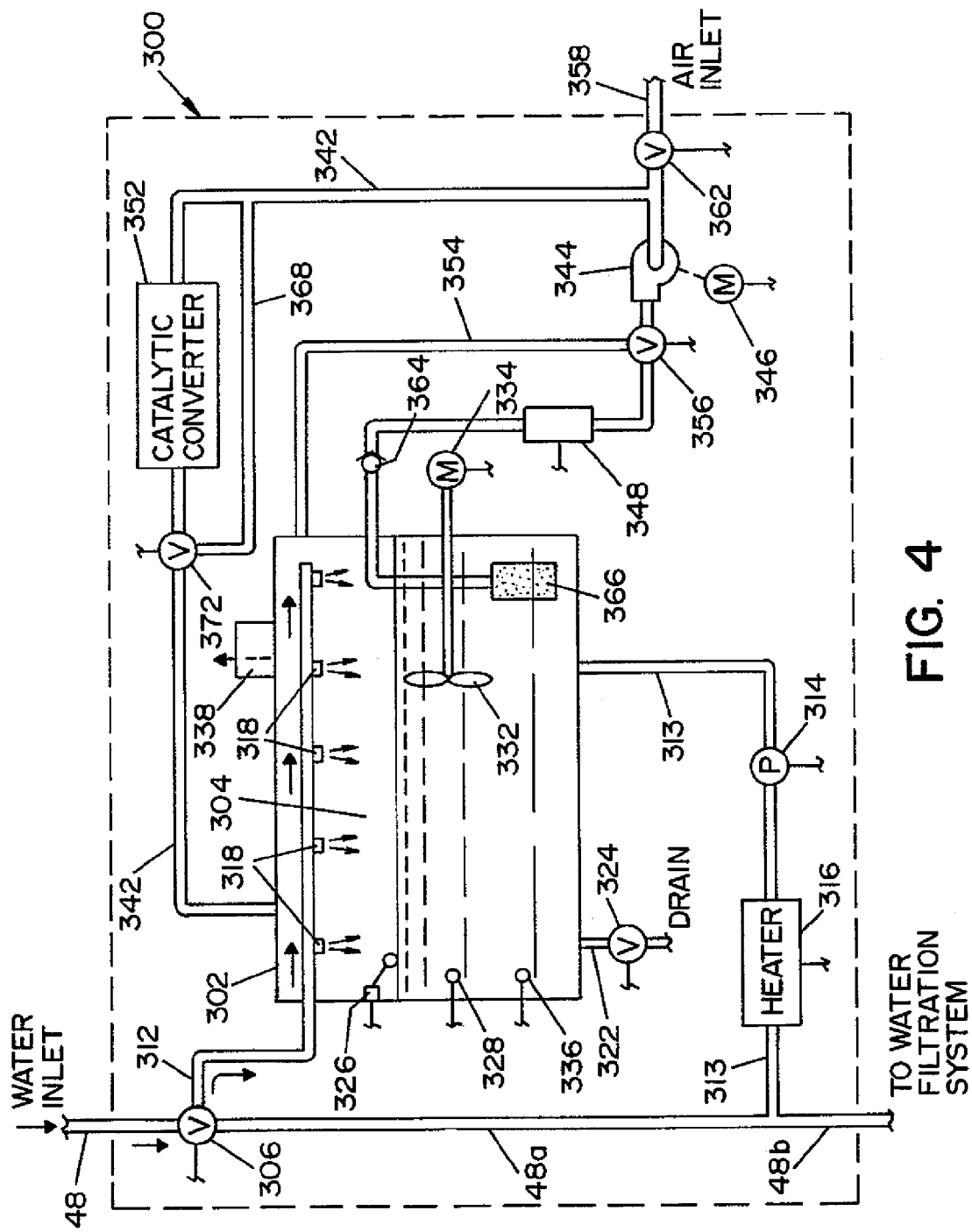
FIG. 4 is a schematic view of a water decontamination system during a fill phase.

The system controller initiates a fill phase of water decontamination system 300 by causing cold water valve 43 to move to a position wherein cold water line 42b is in fluid communication with water inlet line 42. Valve 306 then moves to a position wherein second water inlet line 48 is in fluid communication with inlet line 312. Water entering decontamination system 300 initially flows through filter elements 44, 46. The water then flows through second water inlet line 48 to valve 306, through inlet line 312, through nozzles 318 and into tank 302, as shown by arrows in FIG. 4. As the water fills tank 302, the pressure of the gas in tank 302 increases until pressure-compensating device 338 allows the pressurized gas to escape. Water continues to fill tank 302 until fill switch 326 detects that the desired volume has been achieved. At this time fill switch 326 sends a signal to the system controller. The system controller then causes cold water valve 43 to move to a position wherein flow from the cold water source to second water inlet line 48 is prevented. The system controller also causes valve 306 to move to a position wherein flow from second water inlet line 48 to inlet line 312, is prevented. When valve 306 is in this position, second water inlet line 48 no longer communicates with portion 48a or inlet line 312, but inlet line 312 is in fluid communication with portion 48a. In this respect, the flow of water into tank 302 is terminated and tank 302 is filled with water that is less than about 43° C. As stated above, valve 308 is in a closed position. Based on the positions of valve 306 and valve 308 a water circulation path is formed. The water circulation path is defined by inlet line 312, tank 302, outlet line 313 and portion 48a of second water inlet line 48.

The foregoing description basically describes a fill phase of water decontamination system 300. In one embodiment, second water inlet line 48, inlet line 312 and tank 302 are dimensioned such that the above described fill phase occurs in less than about five (5) minutes.

Figure 5:
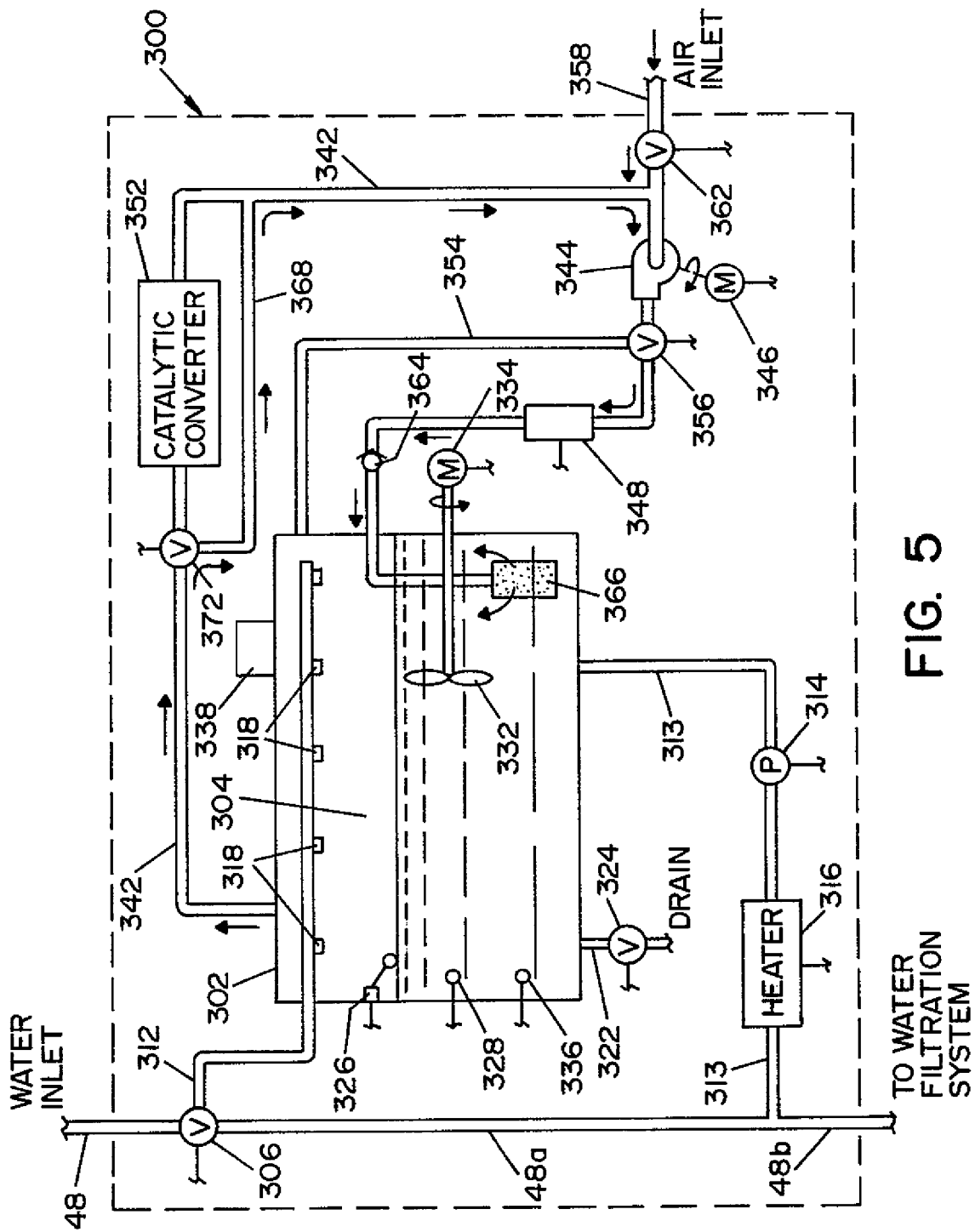
FIG. 5. is a schematic view of a water decontamination system illustrating an ozone introduction phase of the water decontamination system.

Once the fill phase is completed, the system controller initiates an ozone generation phase of water decontamination system 300. During the ozone generation phase, the system controller causes gas inlet valve 362 to move to a position wherein gas inlet line 358 is in fluid communication with branch line 342. As stated above, valve 372 is in a first position wherein a portion of branch line 342 upstream of valve 372 is in fluid communication with second bypass line 368. The system controller energizes motor 346 thereby turning blower 344 and causing gas to flow along a first gas circulation path. The first gas circulation path is defined by gas inlet line 358, branch line 342, tank 30, branch line 342 and second bypass 368. Gas flows from gas inlet line 358, through branch line 342, through ozone producing device 348, through directional check valve 364, through ozone dissolution device 366 into tank 302, as shown by arrows in FIG. 5. Blower 344 also causes gas located above the water in tank 302 to flow along branch line 342, through valve 372, through second bypass 368, through branch line 342 to blower 344. In this respect, gas containing ozone, located above the water in tank 302, is circulated back to the inlet of blower 344 to be reintroduced into water in tank 302. By not destroying ozone in the gas located above the water in tank 302, the concentration of ozone in the water in tank 302 is rapidly increased. In the embodiment wherein ozone dissolution device 366 is a metal or ceramic filter, the second end of branch line 342 is located within cavity 304 below the water level of water in tank 302. In this respect, gas flowing through ozone dissolution device 366 forms small bubbles of gas in the water in tank 302. The creation of small bubbles of gas aids in the dissolution of the gas into the water in tank 302.

During the ozone generation phase, the system controller energizes ozone producing device 348 thereby causing ozone to be introduced into the gas flowing therethrough. In this respect, ozone is transported to gas dissolution device 366 where it is bubbled into water in tank 302. As stated above, the water in tank 302 is below about 43° C. As ozone is insoluble in water if the temperature of the water is above 43° C., the bubbling of ozone into the water in tank 302 dissolves ozone in the water in tank 302. The bubbles created by ozone dissolution device 366 are small and aid in the dissolution of ozone into the water in tank 302. The system controller also energizes agitating device 332 to a first "ON" state to achieve a uniform concentration of dissolved ozone therein. As stated above, the first "ON" state of agitating device 332 allows for circulating of the water in tank 302 in a gentle manner to circulate the water therein without severely agitating the water. Severe agitation or circulation of the water in tank 302 may cause the ozone dissolved in the water to come out of solution. The foregoing description basically describes an ozone generation phase of water decontamination system 300. The ozone generation phase continues until the concentration of ozone in the water in tank 302, as measured by sensor 328, has achieved a predetermined concentration. In one embodiment, ozone-producing device 348 is dimensioned to increasing the concentration of ozone in tank 302 to between about 0.1 mg/L to about two (2) mg/L in between about five (5) to about ten (10) minutes.

Once the ozone generation phase is completed, the system controller initiates an exposure phase in water decontamination system 300. The purpose of the exposure phase is to reduce the viral level in the water in tank 302 to a desired level. Table 1 below provides a list of typical viruses and a concentration of ozone and the time required to deactivate the listed number of virus. The information in Table 1 was provided by Ozone Safe Food, Inc. on the web site http://www.ozonesafefood.com/ozone_in_drinking_water_treatment.pdf.

TABLE 1

| Virus | Dosage ($O_3$, mg/L) | Time (minute) | Log Reduction ($10^x$) |
|---|---|---|---|
| Adenovirus, 7A | 0.30 | 3.0 | 4 |
| Echovirus 5, 12 & 29 | 0.40 | 4.0 | 4 |
| Enterovirus, over 35 types | 0.30 | 4.0 | 4 |
| Coxsackie B3 & B5 | 0.60 | 1.0 | 4 |
| Poliovirus 1, 2 & 3 | 0.30 | 4.0 | 4 |
| Most other viruses | 0.40 | 4.0 | 4+ |

The reduction of viruses in water is typically stated in terms of logs of reduction, or a log reduction value (LRV) of viruses. For example, the decontamination of $10^6$ viruses corresponds to a six (6) log reduction or a log reduction value of six (6). To achieve a predetermined log reduction value, water decontamination system 300 either maintains a predetermined ozone concentration for a predetermined duration, or the system controller continuously calculates the cumulative log reduction value during the exposure phase and terminates the exposure phase when the desired log reduction value is achieved. For either method, the system controller maintains motor 346, ozone-producing device 348 and agitating device 332 energized during the exposure phase. In a preferred embodiment wherein a predetermined concentration is maintained for a predetermined duration, the duration of the exposure phase is about thirty (30) minutes. For a given volume of water in tank 302, ozone-producing device 348 is capable of producing enough ozone to result in a concentration of ozone in tank 302 of about 0.1 mg/L to about two (2) mg/L for about thirty (30) minutes.

In the embodiment wherein the system controller calculates a cumulative log reduction value during the exposure phase, the system controller uses sensor 328 to determine the concentration of ozone in water in tank 302. Based on a given concentration of ozone for a given period of time, the system controller calculates the log reduction achieved for that time period. The system controller continues to monitor sensor 328 during the exposure phase to calculate the log reduction value for discrete periods of time. Once the sum of the log reduction for each discrete period of time is greater than or equal to a desired log reduction, the system controller terminates the exposure phase.

Figure 6:
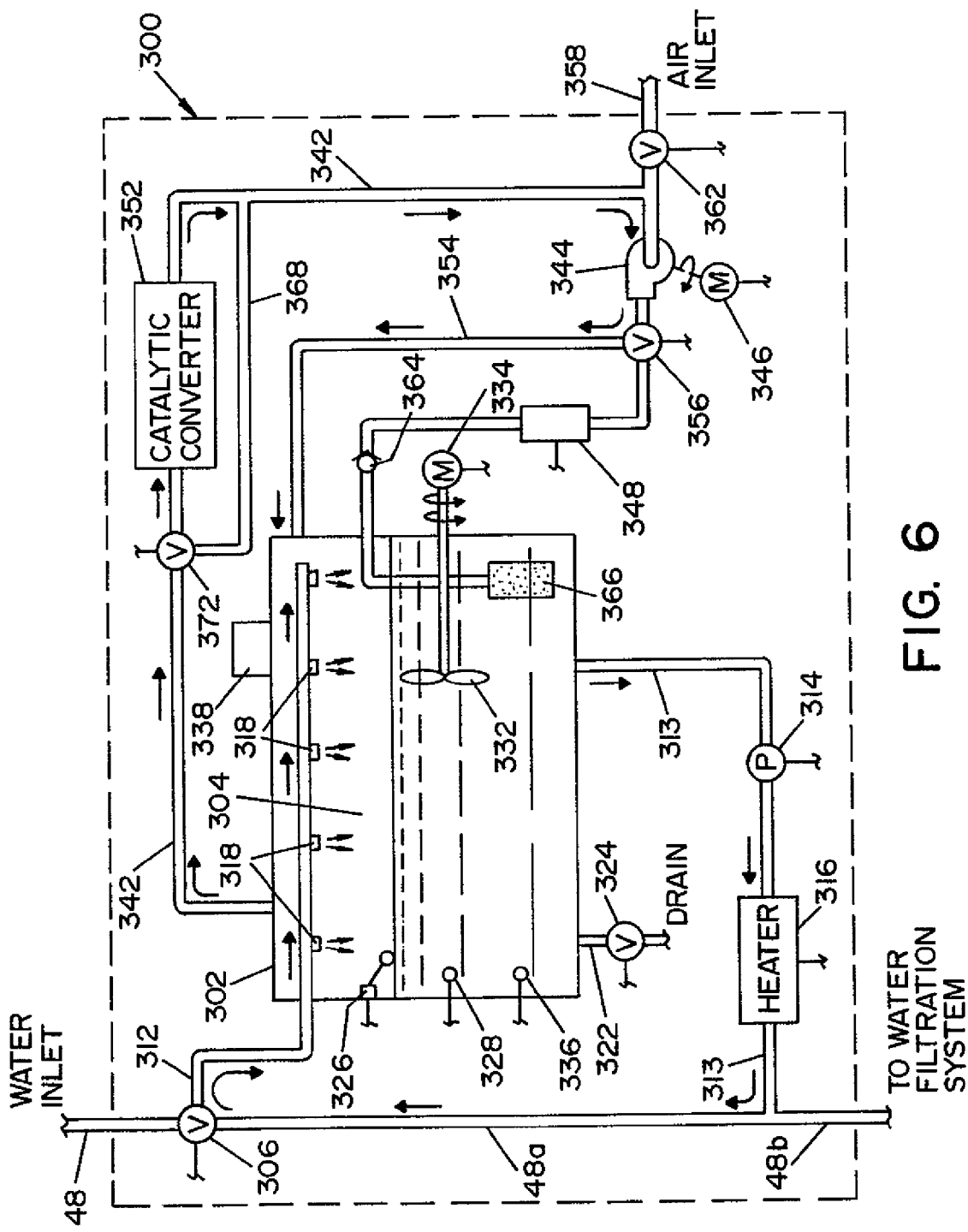
FIG. 6 is a schematic view of a water decontamination system illustrating an ozone destruction phase and a holding phase of the water decontamination system.

After the exposure phase is completed, the system controller initiates an ozone destruction phase of water decontamination system 300. During the ozone destruction phase, the system controller turns ozone producing device 348 off to stop the introduction of ozone into gas flowing therethrough. The system controller also energizes pump 314 to circulate between about three (3) and about four (4) gallons per minute through outlet line 313. In this respect, water flows along the water circulation path from pump 314, through outlet line 313, through portion 48*a* of second water inlet line 48, through valve 306, through inlet line 312, through nozzles 318 to tank 302, as shown in FIG. 6. As water flows through nozzles 318 jets of high velocity water are produced that impinge on water located in tank 302. The impingement of the jets agitates the water therein thereby aiding in ozone removal from the water in tank 302. The system controller also energizes heating device 316 to heat water flowing therethrough. The system controller controls heating device 316 to achieve a predetermined temperature for the water in tank 302. An increase in water temperature reduces the amount of ozone that can be dissolved in it. Therefore, an increase in water temperature will aid in the removal of ozone from the water in tank 302. At a temperature of about 43° C. and higher, the solubility of ozone in water drops to nearly zero. Thus in one embodiment, the water in tank 302 is increased to a temperature between about 40° C. to about 55° C. In another embodiment, the water is heated to a temperature between about 42° C. to about 50° C. In yet another embodiment the water is heated to a temperature of between about 43° C. to about 48° C. In another embodiment the water is heated to about 43° C. In yet another embodiment the water is heated to about 44° C. In still yet another embodiment the water is heated to about 45° C. The system controller also causes agitating device 332 to operate at a second "ON" state wherein water in tank 302 is highly agitated. The increased agitation of water in tank 302 further aids in removing ozone from water in tank 302.

The system controller moves valve 372 to a second position wherein a portion of branch line 342 upstream of valve 372 is in fluid communication with ozone destruction device 352 and not second bypass line 368. The system controller also moves valve 356 to a first position wherein first bypass line 354 is in fluid communication with a portion of branch line 342 upstream of valve 356. In this respect, a second gas circulation path is formed. The second gas circulation path is defined by gas inlet line 358, branch line 342, first bypass line 354, tank 302, tank 30 and branch line 342. As the ozone in the water escapes it is forced along branch line 342 to ozone destruction device 352 wherein the ozone is destroyed, as shown in FIG. 6. The system controller continues to monitor sensor 328 to determine when a desired concentration of ozone in the water in tank 302 is achieved. According to one aspect of the present invention, the system controller monitors sensor 328 to determine when a concentration below about 0.03 mg/L is achieved. In one embodiment, the removal of ozone from the water takes between about five (5) to about fifteen (15) minutes.

The foregoing description basically describes an ozone destruction phase of water contamination system 300. In one embodiment, heating device 316, agitating device 332, pump 314, ozone destruction device 352 and blower 344 are all dimensioned such that the above describe ozone destruction phase occurs in about thirty (30) minutes. Hereinafter, water treated during the exposure phase shall be referred to as "treated water."

The ozone destruction phase is followed by either a delivery phase or a holding phase. In the event that apparatus 10 is not ready to be filled with treated water, the system controller initiates a holding phase of decontamination system 300. During the holding phase, the system controller continues to energize pump 314, heater 316, agitating device 332, ozone destruction device 352 and blower 344. In this respect, fluid continues to circulate throughout water decontamination system 300 as shown in FIG. 6. The system controller thereby maintains the water decontamination system 300 in a holding phase until apparatus 10 is ready to initiate a rinse phase.

Figure 7:
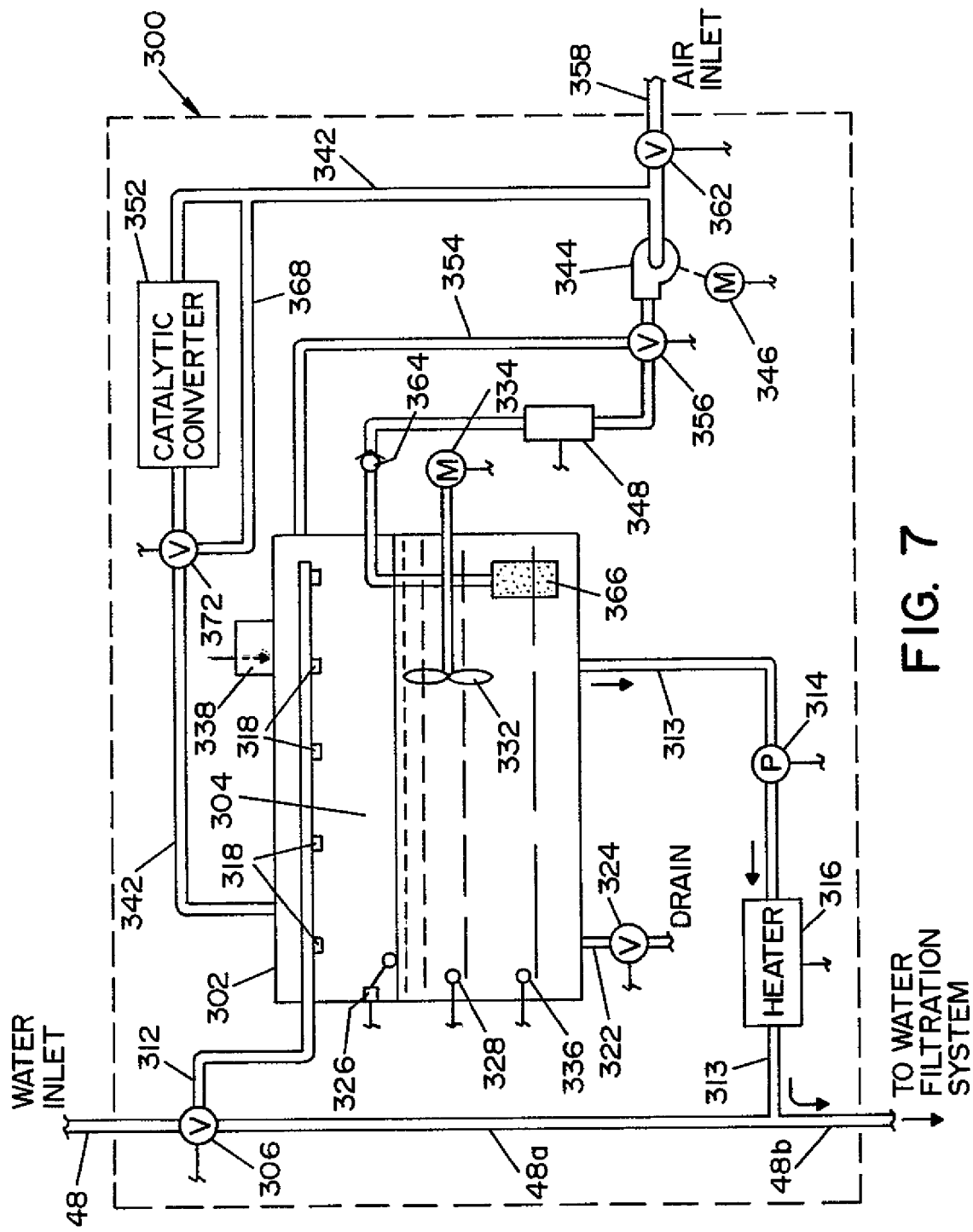
FIG. 7 is a schematic view of a water decontamination system illustrating a delivery phase of the water decontamination system.

When rinse water is required by apparatus 10, the system controller initiates a delivery phase of water decontamination system 300. Prior to initiating the delivery phase, the system controller de-energizes blower 344, ozone destruction device 352, heater 316 and agitating device 332. During the rinse phase of apparatus 10, the system controller energizes valve 308 to a condition wherein second water inlet line 48 is in fluid communication with system feeder line 62. The system controller also causes valve 306 to move to a state wherein fluid does not flow through valve 306. Pump 314 is energized to force treated water from tank 302, through outlet line 313, through second portion 48b of inlet line 48, through valve 308 and into system feeder line 62, as shown in FIG. 7. As shown in FIG. 7, make-up gas enters tank 302 through pressure compensation device 338. As stated above, pressure compensation device 338 includes a filter membrane to filter out debris and contamination from gas flowing therethrough. In this respect, the gas entering tank 302 during a delivery phase is free of contamination. The treated water entering apparatus 10 from water decontamination system 300 enters circulation system 40. The treated water is then filtered by filter assemblies 110, 130 in feeder line 62 and proceeds to fill circulation system 40, chamber 36 and container 26.

Check valve 174 between water inlet valve 54 and filter bypass line 172 causes all of the incoming water to flow through the first and second filter assemblies 110, 130, thereby insuring filtration of the treated water flowing into apparatus 10.

The treated water forces air in fluid circulation system 40, chamber 36 and container 26 to an over-flow/air device (not shown) that is typically located at the highest point of apparatus 10. Air within the system migrates toward the over-flow device.

The presence of the treated water flowing through the over-flow block is indicative that apparatus 10 is filled with water. The system controller then causes valve 308 to close, thereby stopping the flow of water from decontamination system 300 into apparatus 10, i.e., into fluid circulation system 40, chamber 36 and container 26. Valve 306 also moves to a state wherein inlet line 312 and portion 48a of inlet line 48 are in fluid communication with each other. The foregoing description basically describes a treated water fill phase of apparatus 10.

Once apparatus 10 is filled, the system controller energizes pump 92 to circulate the treated water through apparatus 10. After a predetermined period of time, the treated water is drained from apparatus 10 as heretofore described.

During the fill, circulation and drain steps of the rinse phase of apparatus 10, the fluid over-flow/air make-up assembly operates to prevent microbial contaminants from entering the internal environment within the system. In one embodiment, pump 314 and outlet line 313 are dimensioned such that the delivery phase of water decontamination system 300 occurs in about two (2) minutes.

The foregoing description describes a rinse phase of apparatus 10 using treated water supplied by water decontamination system 300. It is contemplated that water decontamination system 300 is operated in conjunction with apparatus 10. In this respect, tank 302 in decontamination system 300 is may be dimensioned to allow for efficient operation of apparatus 10. For example, if apparatus 10 performs only one rinse, then the size of tank 302 is large enough to fill apparatus 10 at least once with rinse water. Likewise, if apparatus 10 performs two rinse phases, tank 302 is dimensioned to fill apparatus 10 with rinse water at least twice. If apparatus 10 requires more than one rinse phase, the system controller maintains pump 314, heating device 316 and agitating device 332 energized and repeats the rinse phase of apparatus 10 and delivery phase of water decontamination system 300, as described above. Otherwise, the system controller de-energizes pump 314, heating device 316 and agitating device 332.

Figure 8:
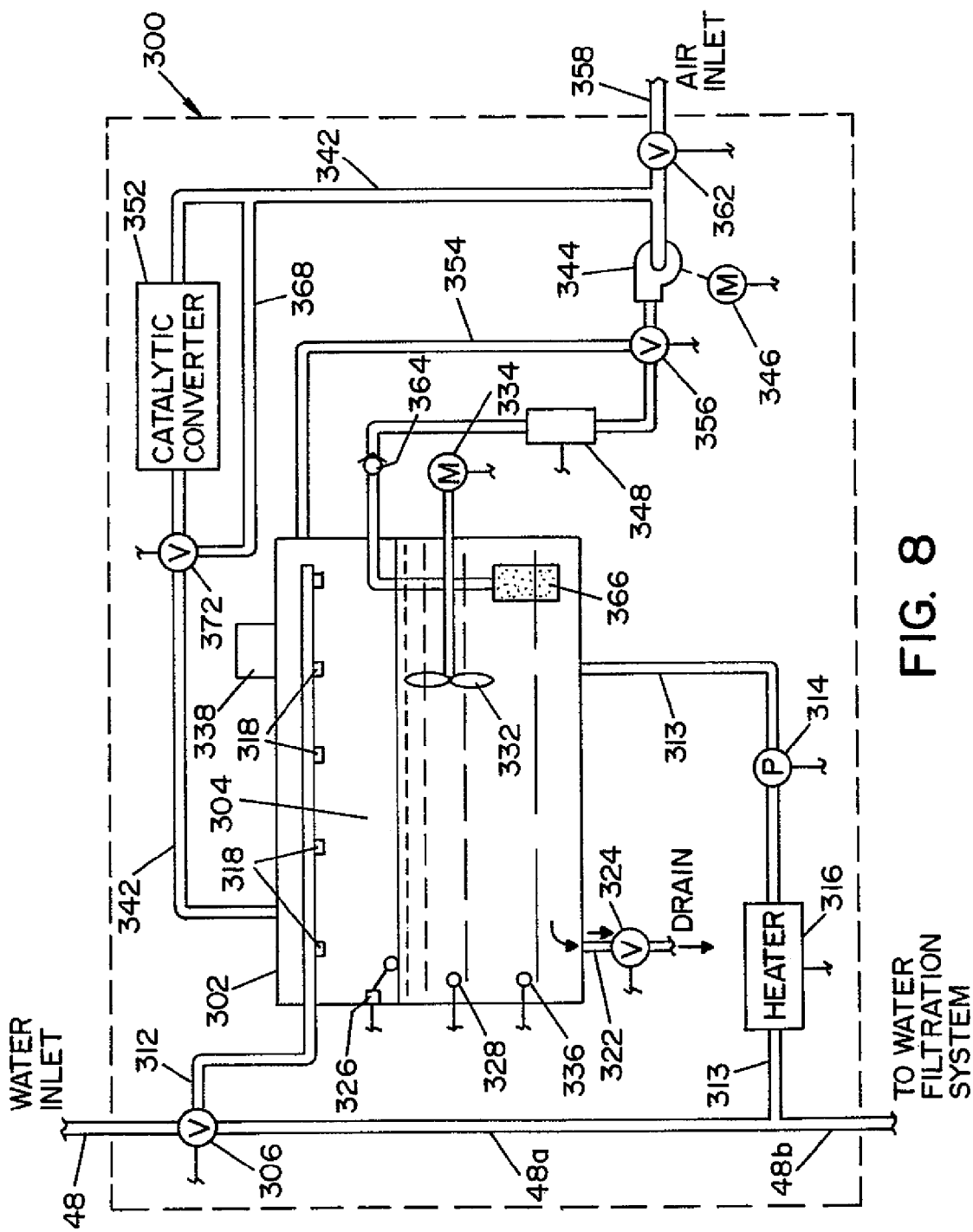
FIG. 8 is a schematic view of a water decontamination system illustrating a drain phase of the water decontamination system.

Following the delivery phase, the system controller initiates a drain phase of water decontamination system 300. The system controller causes drain valve 324 to open thereby allowing any residual fluid in tank 302 to flow through drain line 322 and to a drain, as shown in FIG. 8. In this respect, no residual water remains in tank 302 at the end of the drain phase.

It is contemplated that water decontamination system 300 may also be used to reduce the viral count in water used during the initial fill phase of circulation system 40. In this respect, water decontamination system 300 performs a decontamination cycle prior to the initial fill phase of apparatus 10. Water decontamination system 300 then delivers treated water to apparatus 10 for the initial fill phase of apparatus 10.

It is also contemplated that decontamination cycle of water decontamination system 300 occurs before the fill phase of circulation system 40 or during a fill phase, a chemical introduction and exposure phase, and/or a drain phase of apparatus 10. In either respect, the water decontamination system 300 completes a decontamination cycle prior to apparatus 10 requiring treated water for the rinse phase.

It is intended that all such modifications and alterations be included insofar as they come within the scope of the invention as claimed or the equivalents thereof.

Having described the invention, the following is claimed:

1. A method for decontaminated devices in a processor, said processor including a chamber for holding devices to be decontaminated, a circulation system for circulating a liquid sterilant or microbial decontamination fluid through said chamber, said chamber forming a part of said circulation system, a water filtration system for filtering water used in said processor, said water filtration system having a water line connectable to a source of pressurized water and a water decontamination system fluidly communicating with said source of water and said processor, said method comprising the steps of:
   a) circulating a carrier gas along a first closed loop gas circulation path wherein said carrier gas is introduced into a predetermined volume of water, said first closed loop gas circulation path including a primary conduit and a first bypass conduit that bypasses an ozone destruction device;
   b) introducing ozone into said carrier gas as said carrier gas flows along said first closed loop gas circulation path such that said ozone is introduced and dissolved into said predetermined volume of water;
   c) collecting an conveying any ozone that does not dissolve in said water along said first closed loop gas circulation path to reintroduce said ozone back into said water;
   d) establishing a concentration of ozone in said predetermined volume of water between about 0.1 mg/L to about 2 mg/L;
   e) mixing said water and said ozone to achieve a uniform concentration of ozone in said water;
   f) circulating said predetermined volume of water along a closed loop water circulation path;
   g) heating said predetermined volume of water to at least about 40° C.;
   h) mechanically agitating said predetermined volume of water;
   i) circulating said carrier gas along a second closed loop gas circulation path wherein said second closed loop gas circulation path includes said primary conduit, said ozone destruction device, and a second bypass conduit that bypasses an ozone producing device and wherein said ozone separated from said water is conveyed by said carrier gas along said second closed loop gas circulation path;
   j) destroying said ozone conveyed by said carrier gas with said ozone destruction device along said second closed loop gas circulation path, said ozone destruction device being downstream from said predetermined volume of water;
   k) continuing steps f), g), h), i), and j) until the concentration of said ozone in said predetermined volume of water is below about 0.03 mg/L and until said ozone in said carrier gas is destroyed; and
   l) conveying said water to said chamber following a decontamination cycle to rinse said devices disposed in said chamber.

2. A method for decontaminating devices as defined in claim 1, wherein said step a) of introducing includes bubbling said gas containing said ozone into said predetermined volume of water.

3. A method for decontaminating devices as defined in claim 1, wherein said water in said step a) is between about 20° C. and about 40° C.

4. A method for decontaminating devices as defined in claim 1, wherein said step j) includes a catalytic ozone destruction device located in said second closed loop, gas circulation path.

5. A method for decontaminating devices as defined in claim 1, wherein said step g) of heating includes a heating element located along said closed loop water circulation path.

6. A method for decontaminating devices as defined in claim 1, wherein said step h) of mechanically agitating includes mixing said water in a tank located in said closed loop water circulation path.

7. A method of reducing viral levels in water used in a processor for decontaminating device, said method comprising the steps of:
   a) circulating a carrier gas along a first closed loop gas circulation path wherein said carrier gas is introduced into a predetermined volume of water, said first closed loop gas circulation path includes a primary conduit and a first bypass conduit that bypasses an ozone destruction device;
   b) introducing ozone into said carrier gas as said carrier gas flows along said first closed loop gas circulation path such that said ozone is introduced and dissolved into said predetermined volume of water;
   c) collecting and conveying any ozone that does not dissolve in said water along said first closed loop gas circulation path to reintroduce said ozone back into said water;
   d) establishing a concentration of ozone in said predetermined volume of water between about 0.1 mg/L to about 2 mg/L;
   e) mixing said water and said ozone to achieve a uniform concentration of ozone in said water;
   f) circulating said predetermined volume of water along a closed loop water circulation path;
   g) heating said predetermined volume of water to at least about 40° C.;
   h) mechanically agitating said predetermined volume of water;
   i) circulating said carrier gas along a second closed loop gas circulation path wherein said second closed loop gas circulation path includes said primary conduit, said ozone destruction device, and a second bypass conduit that bypasses an ozone producing device and wherein said ozone separated from said water is conveyed by said carrier gas along said second closed loop gas circulation path;
   j) destroying said ozone conveyed by said carrier gas with said ozone destruction device along said second closed loop gas circulation path, said ozone destruction device being downstream from said predetermined volume of water; and
   k) continuing steps f), g), i), and j) until the concentration of said ozone in said water is below about 0.03 mg/L and until said ozone in said carrier gas is destroyed.

8. A method of reducing virus levels in water as defined in claim 7, wherein said step a) of introducing includes bubbling said gas containing said ozone into said predetermined volume of water.

9. A method of reducing virus levels in water as defined in claim 7, wherein said water in said step a) is between about 20° C. and about 40° C.

10. A method of reducing virus levels in water as defined in claim 7, wherein said step j) includes a catalytic ozone destruction device located in said second closed loop gas circulation path.

11. A method of reducing viral levels in water as defined in claim 7, wherein said step g) of heating includes a heating element located along said closed loop water circulation path.

12. A method of reducing viral levels in water as defined in claim 7, wherein said step h) of mechanically agitating includes mixing said water in a tank located in said closed loop water circulation path.

* * * * *

UNITED STATES PATENT AND TRADEMARK OFFICE
CERTIFICATE OF CORRECTION

| | | |
|---|---|---|
| PATENT NO. | : 8,025,807 B2 | Page 1 of 1 |
| APPLICATION NO. | : 12/015036 | |
| DATED | : September 27, 2011 | |
| INVENTOR(S) | : Michael A. Centanni, Kathleen A. Fix and Christopher A. Jethrow | |

It is certified that error appears in the above-identified patent and that said Letters Patent is hereby corrected as shown below:

Column 17, line 16, the word "decontaminated", should read --decontaminating--; line 37, the word "an", should read --and--.

Column 18, line 23, the word "device", should read --devices--; line 28, the word "includes" should read --including--; line 63, the phrase "steps f), g), i), and j)" should read --steps f), g), h), i), and j)--.

Signed and Sealed this
First Day of November, 2011

David J. Kappos
*Director of the United States Patent and Trademark Office*